United States Patent
McGovern et al.

(10) Patent No.: US 12,207,808 B2
(45) Date of Patent: Jan. 28, 2025

(54) TENDON HARVESTING SYSTEM

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Paul McGovern, Hanson, MA (US); Chun Liu, Brookline, MA (US); Christopher David MacCready, Medfield, MA (US); Ali Hosseini, Quincy, MA (US); Timothy Young, Natick, MA (US); Geoffrey Ian Karasic, Raynham, MA (US)

(73) Assignees: Smith & Nephew, Inc., Memphis, TN (US); Smith & Nephew Orthopaedics AG, Zug (CH); Smith & Nephew Asia Pacific Pte. Limited, Singapore (SG)

( * ) Notice: Subject to any disclaimer, the term of this patent is extended or adjusted under 35 U.S.C. 154(b) by 430 days.

(21) Appl. No.: 17/619,052

(22) PCT Filed: Jun. 15, 2020

(86) PCT No.: PCT/US2020/037792
§ 371 (c)(1),
(2) Date: Dec. 14, 2021

(87) PCT Pub. No.: WO2020/257115
PCT Pub. Date: Dec. 24, 2020

(65) Prior Publication Data
US 2022/0167954 A1   Jun. 2, 2022

Related U.S. Application Data

(60) Provisional application No. 63/036,567, filed on Jun. 9, 2020, provisional application No. 62/959,580, filed
(Continued)

(51) Int. Cl.
*A61B 17/00* (2006.01)
*A61B 17/3205* (2006.01)
(Continued)

(52) U.S. Cl.
CPC .... *A61B 17/00008* (2013.01); *A61B 17/3205* (2013.01); *A61B 2017/0042* (2013.01);
(Continued)

(58) Field of Classification Search
CPC .......... A61B 17/00008; A61B 17/3205; A61B 2017/0042; A61B 2017/00738;
(Continued)

(56) References Cited

U.S. PATENT DOCUMENTS 5,797,940 A * 8/1998 Mawhirt .......... A61B 5/150916
606/167
6,019,774 A * 2/2000 Weiss ............. A61B 17/320036
606/167
(Continued)

FOREIGN PATENT DOCUMENTS

DE   102011109715   2/2013
JP   2010284478 A   12/2010

OTHER PUBLICATIONS

Search Report and WO for PCT/US2020/037792 dated Oct. 5, 2020, 12 pages.

*Primary Examiner* — Richard G Louis
(74) *Attorney, Agent, or Firm* — Norman F. Hainer, Jr.; Kate Ryland Tetzlaff

(57) ABSTRACT

A system for improving graft harvesting including a blade guide (320) having a handle (370) and a guide portion with an elongate slot (330). The system may also include a first blade assembly (750) that slides along the elongate slot (330), the blade assembly (750) having a cutting blade (765) rotatably coupled to a handle (780). The cutting blade (765)
(Continued)

may include a leading cutting edge and a trailing cutting edge. The blade assembly (350, 750) and blade guide (320) may cooperate to control a depth of blade penetration into a tissue, as the blade slides along the elongate slot (330). The blade guide (320) may include means to stabilize the guide with the tissue.

17 Claims, 10 Drawing Sheets

Related U.S. Application Data on Jan. 10, 2020, provisional application No. 62/862,407, filed on Jun. 17, 2019.

(51) Int. Cl.
 *A61B 17/32* (2006.01)
 *A61B 90/00* (2016.01)
(52) U.S. Cl.
 CPC .............. *A61B 2017/00738* (2013.01); *A61B 2017/320052* (2013.01); *A61B 2090/034* (2016.02); *A61B 2090/061* (2016.02); *A61B 2090/08021* (2016.02); *A61B 2090/0811* (2016.02)

(58) Field of Classification Search
 CPC .. A61B 2017/320052; A61B 2090/034; A61B 2090/061; A61B 2090/08021; A61B 2090/0811; A61B 18/1402; A61B 2018/1412; A61B 17/3209; A61B 17/3211; A61B 2017/320064; A61B 2017/32113
 See application file for complete search history.

(56) References Cited

U.S. PATENT DOCUMENTS

| | | | | |
|---|---|---|---|---|
| 6,126,615 | A * | 10/2000 | Allen ..................... | A61B 10/02 |
| | | | | 600/562 |
| 6,200,274 | B1 * | 3/2001 | McNeirney ............ | A61B 90/06 |
| | | | | 604/117 |
| 2003/0171757 | A1 | 9/2003 | Coon et al. | |
| 2004/0006389 | A1 | 1/2004 | Steenlage | |
| 2007/0027463 | A1 | 2/2007 | Neubig | |
| 2008/0221579 | A1 | 9/2008 | Panchbahavi | |
| 2012/0016398 | A1 | 1/2012 | Strickland | |
| 2014/0277020 | A1 | 9/2014 | Koogle et al. | |
| 2015/0057693 | A1 | 2/2015 | Burroughs, III | |
| 2016/0331398 | A1 * | 11/2016 | Foster ................ | A61B 17/3211 |

\* cited by examiner

TENDON HARVESTING SYSTEM

CROSS-REFERENCE TO RELATED APPLICATIONS

This application is a 371 Application based on PCT Application No. PCT/US20/037792 filed Jun. 15, 2020 and titled "TENDON HARVESTING SYSTEM", which claims priority to U.S. Provisional App. No. 62/862,407 filed Jun. 17, 2019 and U.S. Provisional App. No. 62/959,580 filed Jan. 10, 2020, both TENDON HARVESTING SYSTEM, herein incorporated by reference in its entirety.

This application also claims priority to U.S. Provisional App. No. 63/036,567 filed Jun. 9, 2020, entitled METHOD AND APPARATUS FOR GRAFT HARVESTING, herein incorporated by reference in its entirety.

FIELD OF THE INVENTION

The present invention relates to the field of surgery and, more particularly, to instruments and methods of harvesting quadriceps tendons.

BACKGROUND

The quadriceps tendon (QT or Quad Tendon) is regularly harvested as a graft for ligament surgery such as anterior cruciate ligament (ACL) revisions/reconstructions. This tendon is located on the superior aspects of the patella on the anterior aspect of the thigh. Currently graft harvesting from the QT may require large incisions up the longitudinal axis of the femur to cut down to the level of the tendon, resulting in large postoperative scars. Alternatively, strippers are available, offering smaller incisions that may advance blindly in a proximal direction from the knee towards the quadriceps muscle. Care must be taken while harvesting to avoid penetration of the watertight capsule surrounding the knee joint as this would allow saline to extravasate up into the extracapsular region and potentially up in the groin area. Joint pressure may also be lost, and therefore distention and visualization of the knee joint during ACL reconstruction. Since the preferred portion of the QT for harvesting is attached to the capsule with no natural separation plane, there is a need for a system and techniques of harvesting a graft safely, in a reasonable amount of time, while protecting the capsule, providing a consistently good-quality consistently sized graft with high cosmetic results that is simple and easily reproducible. Additionally the consistency of the QT is dense and very fibrous and therefore depth of cut may be difficult to control. This is especially the case if the cutting blade is at the end of an unsupported rod that may be pushed away by the tendon for example. The tendon oftentimes just moves out of the way in lieu of being cut. This tendon resistance requires the surgeon to use a jerking motion in order to cut the tendon. Therefore, there is a need for a blade guide assembly that may be placed directly on tissue and held against the tendon to make reliable axial incisions with a consistent cutting depth.

BRIEF DESCRIPTION OF THE DRAWINGS

For a detailed description of example embodiments, reference will now be made to the accompanying drawings in which.

SUMMARY

Figure 1A:
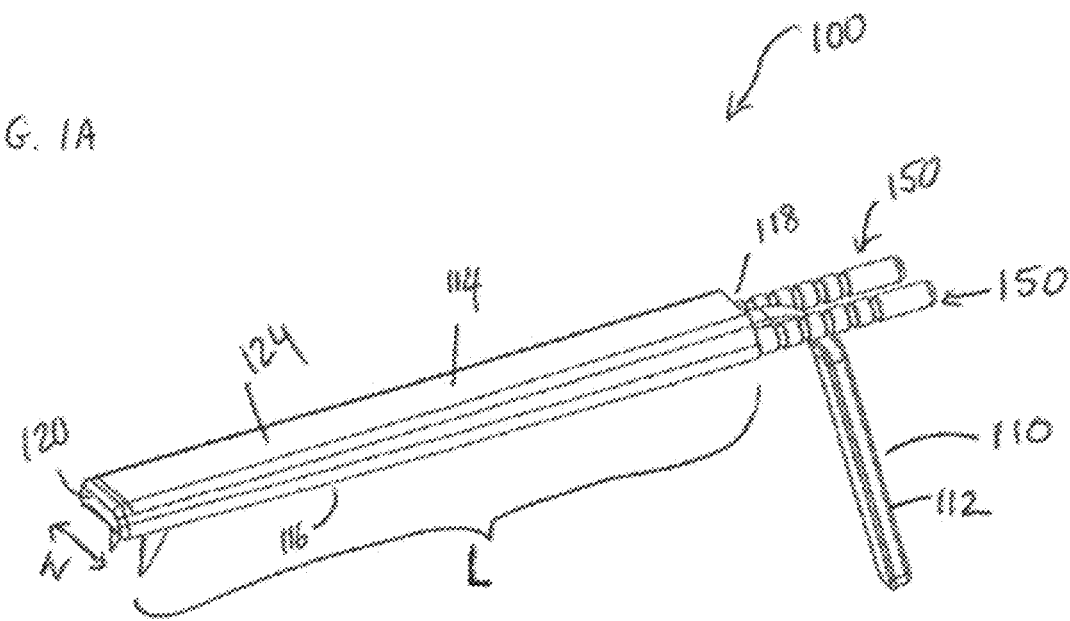
FIG. 1A schematically shows a perspective view of a tendon harvesting system in accordance with at least some embodiments.

Various terms are used to refer to particular system components. Different companies may refer to a component by different names this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Various embodiments are directed to a Quadriceps Tendon (QT) Harvesting System for use in procedures, such as arthroscopic procedures. More particularly, some example embodiments disclosed include a harvesting system for harvesting a target length of tendon tissue including a guide.

The guide has an elongate body defining a handle end and free end and a longitudinal axis. The elongate body also includes an upper and lower surface that defines an elongate body thickness. The elongate body lower surface has a guide slot with a length that extends parallel to the longitudinal axis. The guide slot receives a blade therethrough and guides translation of the blade along the guide slot length and thereby along the tendon tissue. This maintains the blade along a preferred trajectory along the tendon tissue. The guide also limits a cutting depth of the blade into the tendon tissue as the blade translates along this trajectory. In some embodiments, the guide slot may extend from the lower surface up to and including the upper surface, such that the body thickness is configured to limit the blade extension through the slot and thereby limit the cutting depth of the blade into the tendon tissue as the blade translates along the slot length. In some embodiments, the elongate body free end is configured to anchor with the tendon tissue. In some embodiments, the elongate body may include a means to pierce the tendon tissue and thereby anchor with the tendon tissue. In some embodiments, the means to pierce the tendon tissue may include at least two discrete elements extending perpendicular from the longitudinal axis at the guide free end. In some embodiments, the free end may anchor the guide with the tendon tissue with the body in a first and a second orientation; the first and second orientation flipped around the longitudinal axis about 180 degrees relative to each other. In some embodiments, the blade may include a surface that engagingly slides along the body upper surface while translating the blade. In some embodiments, the blade may include a handle, pivotally coupled to the blade that maintain the blade slidingly engaged to the body upper surface while the handle pivots. This allows the blade to be pushed along and under a patient's skin while the handle pivots to slide under the skin also.

In a further embodiment, a harvesting system for harvesting a length of tissue is disclosed. This system includes a blade guide with a handle end and a guide end or portion extending therefrom. The guide end includes an elongate opening. The system also includes a blade assembly having a cutting blade. The blade assembly preferably slides along the elongate opening with the cutting blade extending through the elongate opening. The blade assembly and guide end cooperate to control extension of the cutting blade into the tissue as the blade assembly translates along a length of the elongate opening. In some embodiments, the blade assembly may include a handle, pivotally coupled to the cutting blade such that the handle may rotate through a range of angles relative to the cutting blade while translating the cutting blade along the elongate opening. In some embodiments, the blade assembly may include two cutting blades laterally spaced from each other. In some embodiments, the elongate opening may receive one of the two cutting blades therethrough, placing the other of the two cutting blades along or adjacent a lateral-most outer surface of the blade guide. In some embodiments, the blade guide may include elements that anchor with the tendon tissue. In some embodiments, the blade guide may include at least one tooth extending perpendicularly from a longitudinal axis of the guide slot, configured to anchor with the tendon tissue. In some embodiments, the blade assembly may include a surface that slidingly engages an upper surface of the guide end and controls extension of the cutting blade into the tissue while translating the cutting blade along the elongate opening.

An example method of harvesting a graft is also disclosed including inserting a guide portion of a blade guide through an incision and along an anterior surface of a quadriceps tendon (QT). A first cutting blade of a blade assembly is inserted into a first end of an elongate opening of the guide portion. A surface of the blade assembly is slidingly engaged along the guide portion while advancing the first cutting blade along the elongate opening to a second, opposing end of the elongate opening and thereby cutting a first length of the QT. Maintaining the surface engaged along the guide portion controls the depth of penetration of the first cutting blade into the QT. The first cutting blade may be pivotally coupled to a handle of the blade assembly such that while advancing the first cutting blade the handle may rotate through a range of angles relative to the cutting blade while the cutting blade maintains a constant depth of penetration. The blade assembly may include a second cutting blade parallel to and laterally offset from the first cutting blade, such that advancing the first cutting blade simultaneous advances the second cutting blade and forms two parallel elongate cuts through the QT. The example method may also include anchoring a portion of the guide portion with the QT. The guide portion may be anchored before inserting the first cutting blade.

Additional example embodiments are directed to a system for harvesting a tendon with a blade guide having a handle at a first end and a second end defining a guide portion with an elongate opening extending therefrom. The elongate opening or channel may have an open end adjacent the handle. The system also includes a first blade assembly that may slide along the elongate opening. The elongate opening is configured to allow passage of a cutting blade therethrough, to cut posteriorly into the QT. Cutting blade may rotatably couple to a first blade assembly. The cutting blade may have a leading cutting edge and a trailing cutting edge. The cutting blade may rotate towards a first orientation while advancing along the elongate channel in a first direction to cut tissue at a first depth with the leading cutting edge surface and may also rotate to a different orientation, while retracting the cutting blade along the elongate channel to cut the tissue with the trailing edge surface to a second larger depth. Blade guide may also include second elongate channel or opening parallel to the first elongate channel and laterally spaced therefrom. The first blade assembly may also slide along the second elongate channel to cut through the tendon. Alternatively, the system may include a second blade assembly that may slide along the second elongate channel, the second blade assembly may include a cutting blade rotatably coupled to the second blade assembly, the cutting blade having a leading cutting edge surface and a trailing cutting edge surface. The second blade assembly cutting blade may also rotate to a first orientation while advancing through the second elongate channel so as cut the tissue at a first depth with the leading cutting edge surface and is also configured to rotate to a different orientation, while retracting the second blade assembly cutting blade so as to cut the tissue with the trailing edge surface at a second larger depth. The first and second blade assembly may be each independently slideable along the blade guide. Alternatively the first blade assembly may include two blades laterally spaced from each other, each blade have a leading cutting edge and a trailing cutting edge. One of the two blades may extend through the elongate opening and another of the two blades may extend along a lateral-most outer surface of the blade guide. The leading and trailing cutting edge of each of the two blades may be continuous with each other and form an arc.

A method of harvesting a tendon is also disclosed including inserting an elongate opening or channel of a blade guide through an incision and along an anterior surface of a quadriceps tendon. While the blade guide is held stationary a first blade assembly may be inserted into the elongate channel and advanced along the elongate channel. The first blade assembly may include a cutting blade pivotally coupled to a rod of the first blade assembly. The cutting blade may define a leading and trailing cutting edge and while advancing the first blade assembly, the leading cutting edge may cutting into and along the quadriceps tendon form a first elongate cut having a first depth. The first blade assembly may then be retracted along the elongate channel to cut into and along the first elongate cut with the trailing cutting edge to modify the first elongate cut to have a second depth. While advancing the first blade assembly the cutting blade may be oriented at a first angle relative to the blade guide rod, thereby defining the first depth, and while retracting the first blade assembly the cutting blade may pivot to be oriented at a second angle relative to the blade guide rod, thereby defining the second depth. The cutting blade may extend further into the quadriceps tendon when retracting. The step of inserting may further comprise inserting a second elongate channel of the blade guide through the incision and along an anterior surface of a quadriceps tendon; and inserting a second blade assembly into the second elongate channel and advancing the second blade assembly along the second channel, the second blade assembly having a pivoting cutting blade with a leading and trailing cutting edge and while advancing the second blade assembly, cutting into and along the quadriceps tendon with the leading cutting edge so as to form a second elongate cut having a first depth, the second elongate cut laterally spaced from the first elongate cut and parallel to the first elongate cut. The method may further include retracting the second blade assembly along the second elongate channel to cut into and along the second elongate cut with the trailing cutting edge to modify the second elongate cut to have a second depth.

Alternatively the step of inserting may further comprise inserting a second elongate channel of the blade guide through the incision and along an anterior surface of a quadriceps tendon; and inserting the first blade assembly into the second elongate channel and advancing the first blade assembly along the second channel and while advancing the first blade assembly, cutting into and along the quadriceps tendon with the leading cutting edge so as to form a second elongate cut having a first depth, the second elongate cut laterally spaced from the first elongate cut and parallel to the first elongate cut. The method may further comprise retracting the first blade assembly along the second channel to cut into and along the second elongate cut with the trailing cutting edge to modify the second elongate cut to have a second depth. While advancing the first blade assembly, tension from the quadriceps tendon pivots the cutting blade towards a surface on the rod configured to limit the first angle and thereby define a target first depth of cut. While retracting the first blade assembly, tension from the quadriceps tendon pivots the cutting blade towards a second surface on the rod configured to limit the second angle and thereby define a target second depth of cut.

A surgical system for harvesting a length of tendon tissue is also disclosed, the system including a guide defining an elongate single body, having a distal end portion configured to anchor within the tendon tissue and a blade that slides along the elongate single body. The blade selectively interacts with the guide and includes a distal cutting edge and a proximal cutting edge. The blade is slidingly coupled to the guide so that the blade may reciprocally slide along a length of the guide. The blade may be selectively coupled and disposed along a first lateral-most edge of the guide and a second elongate edge of a guide slot. The blade may comprise two parallel distal cutting edges and two parallel proximal cutting edges that are each laterally spaced from each other that may simultaneously form two parallel cuts along the tendon tissue. The guide may also include an elongate slot and the blade reciprocally slides along a length of the slot. The proximal cutting edge and the distal cutting edge may be continuous to form a single curved cutting edge that lies on a plane parallel to a longitudinal axis of the guide.

A further example embodiment is directed to a surgical instrument for harvesting a target length of tendon tissue including a ruler having a longitudinal axis, a width, a thickness and a distal end portion, the distal end portion configured to anchor the guide with the tendon tissue. A slot may extend through the ruler thickness, the slot having extending parallel to the longitudinal axis, the slot configured to receive a blade therethrough and guide the blade translation along the tendon. The slot length may be at least as long as the target length of tendon tissue. The ruler thickness is configured to limit extension of the blade through the slot and thereby limit the cutting depth as the blade translates along the slot length. In some embodiments, the slot may be offset from the longitudinal axis. In some embodiments the distal end portion may be configured to anchor the guide with the tendon tissue with the ruler in a first and a second orientation, the first and second orientation flipped around the longitudinal axis about 180 degrees relative to each other.

A further example embodiment disclosed is a surgical assembly for harvesting a length of tissue. The assembly includes a blade guide with a handle and a guide portion extending therefrom, the guide portion including an elongate opening extending therefrom. The assembly also includes a blade assembly including a cutting blade, the blade assembly configured to slide long the elongate opening with a cutting blade extending through the elongate opening. The blade assembly defines a first surface configured to slide along a top surface of the blade guide and limit penetration of the cutting blade into the tissue. In some embodiments, the blade assembly may be pivotally coupled to a handle such that the handle may rotate through a range of angles relative to the cutting blade while translating the cutting blade along the opening. In some embodiments, the blade assembly may include two blades laterally spaced from each other. In this case, one of the two blades may extend through the elongate opening and the other of the two blades extends along a lateral-most outer surface of the blade guide. In some embodiments, the first surface defines a flat surface offset and angled relative to a leading edge of the cutting blade.

A further example method of harvesting a graft is also disclosed including inserting a guide track of a blade guide through an incision and along an anterior surface of a quadriceps tendon; inserting a blade assembly into and along the guide track, the blade assembly having a cutting blade that extends through an elongate opening that extends along a length of the guide track; and sliding a first surface of the blade assembly along a top surface of the guide track while advancing the blade assembly and cutting into and along the quadriceps tendon, the first surface configured to limit the depth of penetration of the cutting blade into the quadriceps tendon. In some methods, the cutting blade may be pivotally coupled to a handle of the first blade assembly such that while advancing the blade assembly the handle may rotate through a range of angles relative to the cutting blade. In some methods, the blade assembly may comprise two parallel cutting blades, one of the cutting blades extending through the elongate opening and wherein during the step of advancing, two simultaneous elongate cuts through the tissue may be formed.

A further embodiments of a surgical system for harvesting length of tendon tissue is disclosed including a guide defining an elongate body, having a distal end portion configured to anchor with the tendon tissue in either a first orientation or a second flipped orientation relative to the first orientation and a blade that selectively interacts with said guide, the blade having a first cutting edge surface for inserting though a slot of the guide and a second cutting edge surface parallel to the first cutting edge surface. In some embodiments, the first and second cutting-edge surfaces are laterally spaced from each other to simultaneously form two parallel cuts along the tendon tissue while sliding along the guide. In some embodiments, the blade is pivotally coupled to a handle such that the handle independently pivots relative to the blade while translating the blade along the guide slot.

DETAILED DESCRIPTION

Various embodiments are directed to methods of using a QT Harvesting System. The specification now turns to an example system.

A first example system may include a tendon harvesting system 100, which generally includes a blade guide 110 and at least one blade assembly 150. Blade guide 110 is configured to be placed in contact with the tendon, and to preferably lie along an anterior surface of the tendon extending proximally from the knee capsule. Blade guide 110 thereafter may remain stationary while a sliding blade assembly 150 may slide along a portion of the guide 110 to cut into and along the tendon. The surgeon may create two parallel cuts in the tendon, spaced apart a specific width. Preferably each of the parallel cuts also have substantially similar final lengths and depth. Blade guide 110 may include a handle 112 and guide track 114. Handle 112 is generally configured to aid in placement of guide track 114 on the QT surface and also may aid in maintaining the guide track 114 in contact with or aligned with the QT. As shown, handle 112 may be oriented at an angle that is non-zero relative to the guide track longitudinal axis, and may be substantially close to an orthogonal angle. In alternative embodiments, the inventor envisions other handle embodiments that may be offset from the guide track 114 and approximately parallel to the guide track 114 for example.

Figure 1B:
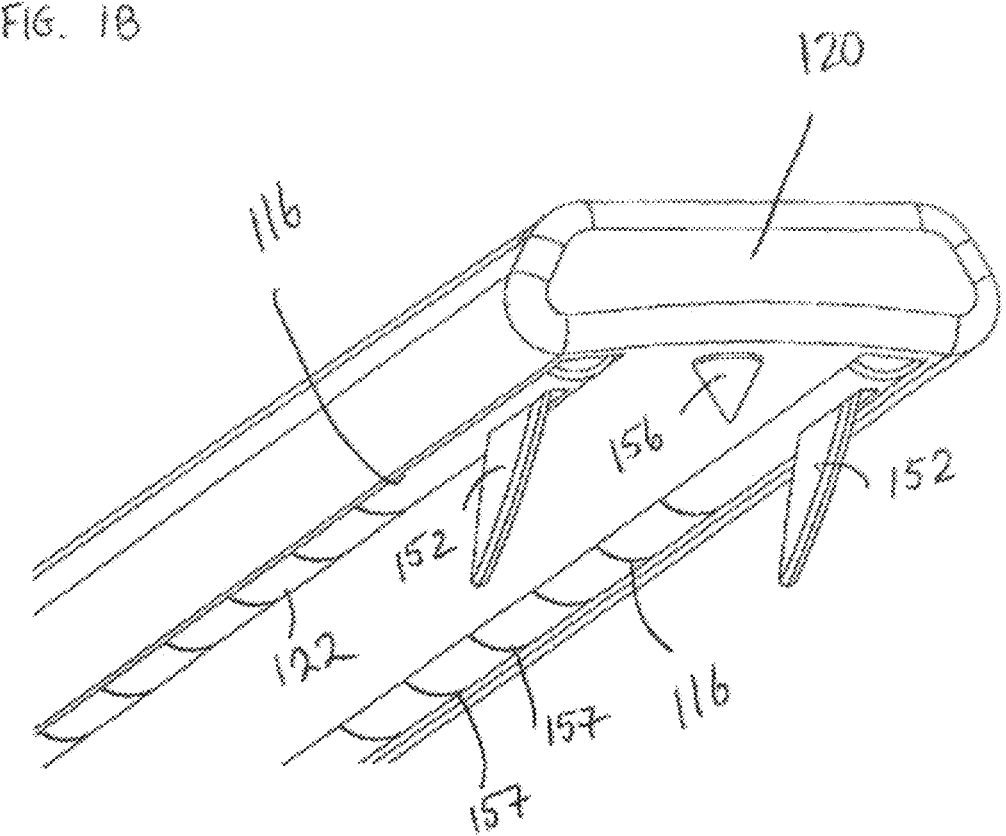
FIG. 1B schematically shows a distal end of a tendon harvesting system in accordance with at least some embodiments.
Figure 1C:
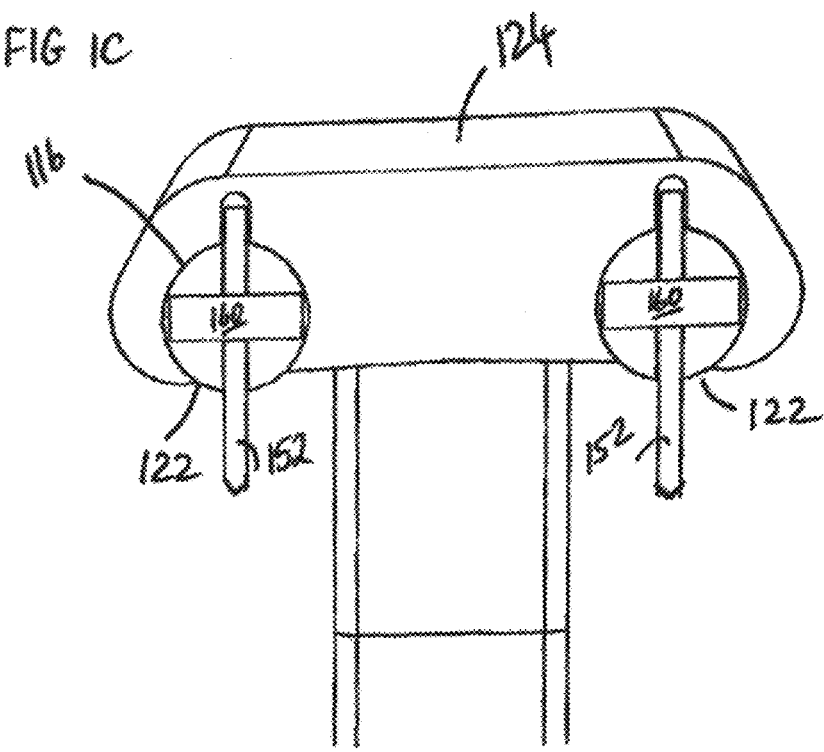
FIG. 1C schematically shows a cross section of a tendon harvesting system in accordance with at least some embodiments.
Figure 1D:
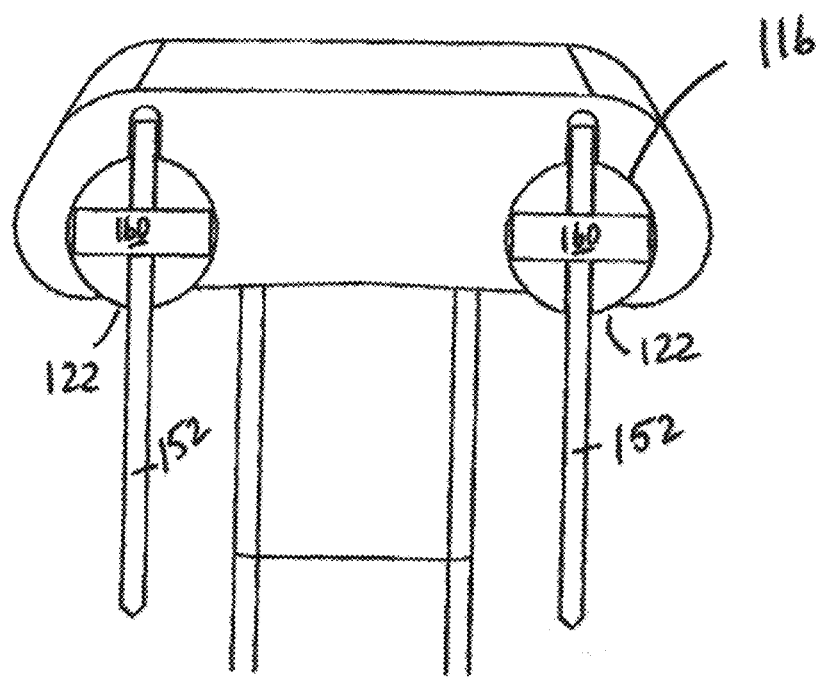
FIG. 1D schematically shows a cross section of a tendon harvesting system in accordance with at least some embodiments.

Guide track 114 defines a length L that is configured to guide the blade assembly 150 and create a desired length of QT graft. In some cases, length L may be shorter than the desired length for the graft, and the blade assembly 150 may extend or slide beyond the end of guide track 114. In some cases length L may be longer than the desired graft length, to accommodate different patients. Guide track 114 also defines a width W that at least partially may define a width of QT graft. Blade guide 110 may come in a series of sizes with varying lengths L and widths W to provide the user options for QT harvest sizing. Guide track 114 may include at least one elongate channel 116, configured to slidingly receive a blade assembly 150. Channel 116 is best seen in FIGS. 1B, 1C and 1D is configured to allow the blade assembly 150 to slide therealong both proximally and distally along channel 116 while maintaining a consistent trajectory of the blade assembly 150. Channel 116 may include an open first end 118 for receiving the blade assembly 150 and may have a closed second end 120 to prevent the blade assembly 150 from extending beyond the guide track. In alternative embodiments, channel 116 may have an open second end 120 to allow the blade assembly 150 to extend farther. Channel 116 may define an elongate slot 122 (best seen in FIG. 1B) along its length, sufficient to allow a cutting blade 152 to extend therethrough, while limiting lateral motion of the cutting blade 152 or rotation of the blade assembly 150 and thereby maintain a controlled pathway for the cutting blade 152 along tissue. Guide track 114 includes two substantially equivalent channels 116 that may be parallel with each other on either side of a longitudinal axis of the guide track 114. This may enable to surgeon to create two elongate parallel cuts either sequentially or simultaneously through the tendon, at a specific width, length and depth. Guide track 114 may lie on a top or anterior surface of the QT and thereby cooperate with a cutting blade 152 to control or limit the depth of cut into the QT. Guide track 114 may include a tooth 156 configured to engage or anchor with an anterior side of QT and limit unintended sliding.

Also shown in FIGS. 1A-1D, blade assembly 150 may include at least one rod 154 with a cutting blade 152 rotatably coupled thereto. Two rods may be provided should the surgeon prefer to make two cuts simultaneously or in staggered relative to each other. Alternatively, one rod may be provided and sequentially placed with each channel 116. Rod 154 may include markings 157 (seen best in FIG. 1B) that may give a length reference to the surgeon. These markings may be axially spaced apart marks and may or may not have numbers indicated next to each markings to indicate a length value. Markings may be known unit distances such as centimetre or inch units, or simply just consistently axially spaced reference marks. Cutting blade, 152 may define a plane that is coaxial with and parallel to the longitudinal axis of rod and pivot along that. Rod 154 is shown with a circular or oval cross section, but may be other cross sections that slidingly fit within a corresponding channel cross-section. Rod 154 may have a first end adjacent the handle 112 that may also include a grip or handle (not shown) to aid advancing and retracting the blade assembly 150. In other embodiments, rod 154 may include a key (not shown) along an outer surface of rod 154 that engages a corresponding or mating keyed channel on an outer surface of guide track 114. The rod key may be inserted and slid along the keyed channel similar to a track or rail system.

FIGS. 1C and 1D shows cross sections of the assembly 100 wherein both cutting blades 152 equally inserted along channel 116 on opposite sides of the track longitudinal axis to each other. FIG. 1C shows the blade in a first orientation such that blade extends a first distance posteriorly from track 114, while cutting blade 152 is advancing towards the distal end. FIG. 1D shows the blade in a second, different angular orientation such that blade extends a second, increased distance posteriorly from track 114, while cutting blade 152 is retracting away from the distal, second end. Both cutting blades 152 may extend through elongate slot 122 on posterior side of guide track 114, and thereby pierce the anterior surface of QT and extend posteriorly. Anterior surface of guide track 114 may be smooth to slide easily under the skin and tissue to gain access to the QT. Of note, while shown axially opposite each other, each blade assembly 150 may be independently operated and in addition, only one blade assembly 150 may be provided, and each cut made sequentially.

Figure 2B:
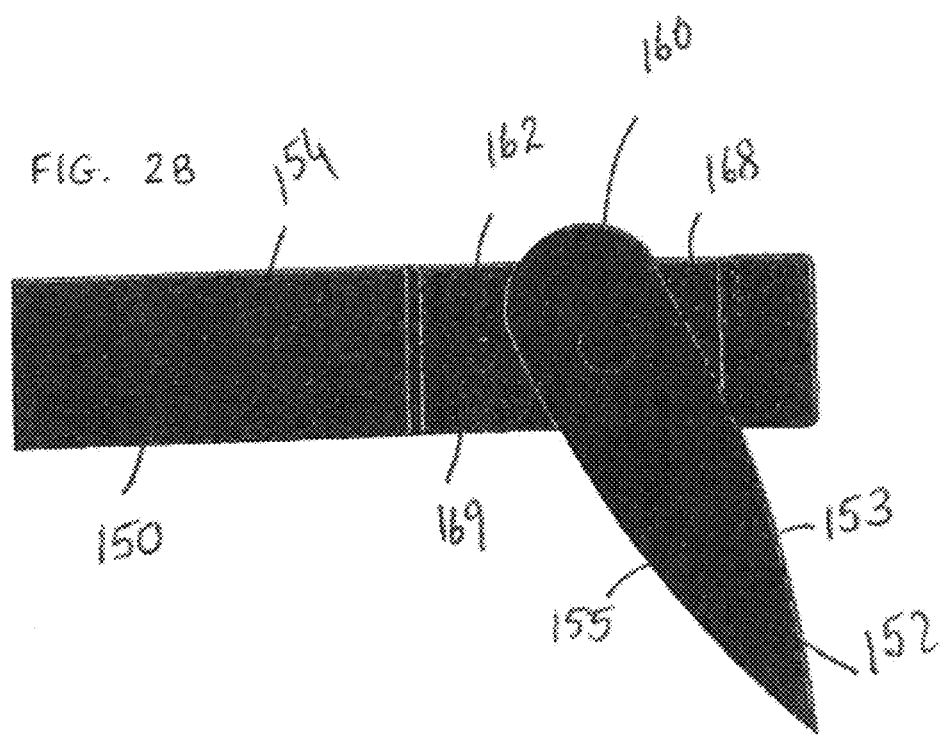
FIG. 2B schematically shows a view of a blade position while retracting the blade assembly of the tendon harvesting system in accordance with at least some embodiments.
Figure 2A:
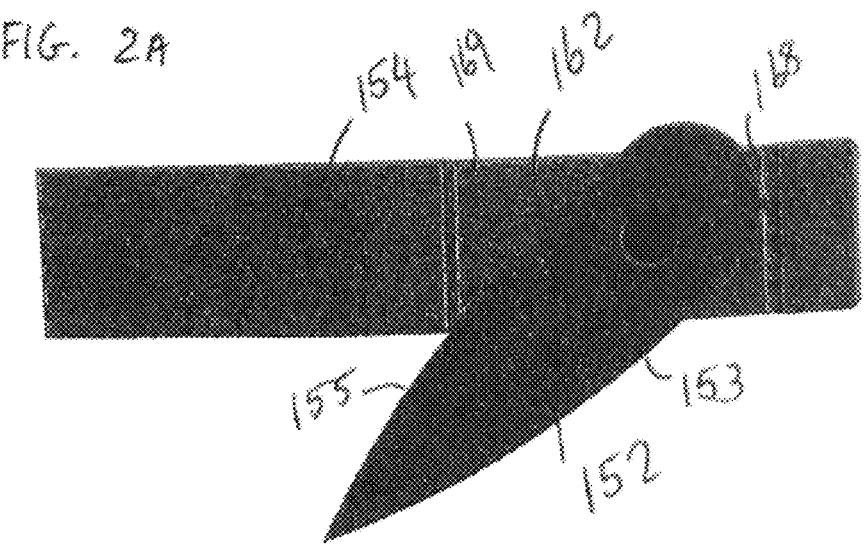
FIG. 2A schematically shows a view of a blade position while advancing the blade assembly of the tendon harvesting system shown in FIGS. 1A-1D in accordance with at least some embodiments.

Best seen in FIGS. 2A and 2B, cutting blade 152 is moveable and more preferably rotatably coupled to rod 154. Rod 154 may include a first elongate opening 162 parallel to the rod longitudinal axis for receiving cutting blade 152 therethrough. Rod 154 may include a plurality of through holes, perpendicular to the first elongate opening to receiving a pin 160. Pin 160 may also extend through a corresponding opening in the blade 152 and may fixedly couple to rod 154, allowing cutting blade 152 to pivot around the axis of the through holes. First elongate opening 162 may define a pocket terminating at a first surface 168 before a second end 170 of rod 154, configured to limit rotation of the cutting blade 152. Furthermore the pocket may define a second surface 169 configured to limit rotation of cutting blade 152 in a second direction. Cutting blade 152 defines a first or leading cutting edge 153 along a first advancing edge of cutting blade and a second or trailing cutting edge 155 along a retracting edge of cutting blade. First cutting edge 153 and second cutting edge 155 may extend towards each other coming together at a pointed end of blade 152. The two cutting edges allow the cutting blade 152 to slice through the tendon while both advancing and retracting along guide track 114. In addition as shown in FIG. 2A, the cutting blade 152 is configured to pivot to an advancing configuration, wherein the cutting blade 152 is oriented at a first angle relative to a longitudinal axis of the rod. The first angle is limited by the second pocket surface 169 and defining a first target depth of cut by the advancing cutting edge 153 into the tendon tissue. The cutting blade 152 is further configured to pivot to a retracting angle configuration shown in FIG. 2B, wherein the cutting blade 152 is oriented at a second angle relative to a longitudinal axis of the rod 154. The second angle is limited by the first pocket surface 168 and defining a second target depth of cut into the tendon tissue, the second target depth of cut larger than the first.

According to an exemplary method of the present invention, a graft may be harvested (sized and cut to specific dimensions) according to the following steps: firstly a small incision may be made above the knee cap of knee; then the guide track 114 may be inserted through the incision, under the skin and along an anterior surface of the QT. The guide track 114 may be advanced proximally along the QT with the use of handle 112. Guide track 114 may be fixed in location using fixing means. A first blade assembly 150 may be inserted into a first channel 116 of guide track 114 and advanced along the first channel, the first blade assembly 150 having a pivoting cutting blade 152 defining a first cutting edge along a first side of the blade and a second cutting edge along a second side of the blade. While advancing the rod 154, cutting blade 152 may be pushed by the tendon towards a first angular orientation, and thereby forming a cut posteriorly into the QT at a first depth with the first cutting edge. The first blade assembly may then be retracted along the first channel 116. While retracting, cutting blade 152 may be pushed by the tendon towards a second angular orientation, and thereby form a cut posteriorly into the QT at a second depth with the second cutting edge. The cutting blade 152 extends further into the tissue when in the second angular orientation. Thus the blade assembly 150 may be configured to cut while both moving away from or towards the knee. A cavity or pocket within the rod may define a plurality of surfaces on the rod 154 to limit the angular orientation of the cutting blade 152. This plurality of surfaces may be surfaces of a cavity within the rod 154 that partially nests the cutting blade 152. A first surface 169, that defines a proximal end of the cavity 162 may limit the cutting blade to a first angular orientation relative to the rod longitudinal axis, and a second surface 168 may limit the cutting blade to a second angular orientation relative to the rod longitudinal axis. A second blade assembly 150 may be inserted into a second channel 116 of guide track 114, the second channel parallel with the first channel and laterally spaced therefrom. Alternatively, the first blade 150 may be first removed from the first channel and then inserted into the second channel. Blade assembly 150 may also be advanced and retracted to as to partially cut into a QT to form two parallel cuts into the QT defining a QT graft width and depth.

A second example embodiment is shown in FIGS. 3A-3C and FIG. 4A-4B. Similar to the previous embodiment, this system 300 generally includes a blade guide 320 and blade assembly 350 selectively coupled to the guide 320. Guide 320 is generally an elongate slotted member having a first handle end 322 that may include a handle 370 and a second end 324. Handle 370 may be pivotally coupled to second end 324. Guide 320 may include a means to engage or anchor with tissue disposed along its length, configured to inhibit the guide 320 from unintentionally sliding or migrating over the tendon during use. As shown guide 320 includes at least one tooth 325 at the second end 324. Having the tooth 325 at an end of the guide 320, rather than along the length may be preferable to limit any potential damage caused by the tooth 325 to the graft to an area that may be easily removed or not form part of the graft itself and therefore maintain good viability of the resulting graft. Guide may further include at least one hole or opening 372. Hole(s) 372 are configured to receive a guide wire, needle or pins (not shown) therethrough and stabilise guide 320. Needles or pins may extend through patient's skin and then through hole(s) 372. Guide second end 324 may be a single component including a distal perpendicularly oriented tooth 325 for engaging with tissue. Tooth 325 may be configured to pierce the tendon, and may have a length X extending from a posterior surface 332 of guide 320 approximately equivalent to or less than a targeted graft thickness. In some embodiments this may be stated alternatively in that the at least one tooth length X may be approximately the same as a blade extension (Y) below the posterior surface 332 of guide 320. Alternative embodiments may include a plurality of teeth. In addition, a high friction surface along a portion of posterior surface of guide 320 in addition to or instead of teeth may aid in maintaining the location or guide 320 on the slippery anterior surface of QT Guide 320 may also include a series of marks 328 on a top surface 326, indicating inches or some equivalent measurement units for visual feedback on a depth of insertion of the guide 320 into an incision and along the tendon. Marks 328 may also be used for estimating a graft cut length and therefore may indicate distances along the elongate slot or opening 330 and not from a distal-most end of guide 320. As shown slot 330 does not necessarily originate from the distal-most end of guide 320; end 331 is spaced away from end. For example in use, during insertion of guide 300 between tissues and over the QT, mark 328 corresponding with the desired graft length may be aligned with the superior pole of the patella and the at least one tooth 325 may then be anchored with an adjacent portion of the tendon tissue. Pins or needles may also be place through holes 372 to further anchor the guide 320.

Slot 330 may extend through the entire thickness T of the guide 320. Slot 330 may aid in maintaining a direction and trajectory of a blade assembly 350. Slot 330 may be sufficiently wide to receive a portion of blade assembly 350 therethrough and allow blade assembly 350 to move there along. Slot 330 may however be sufficiently narrow to limit lateral motion of blade 350 while the blade slides. Slot 330 as shown may extend along a portion of the guide 320, similar to the guide track portion described in earlier embodiments. The slot 330 may be biased or disposed towards a half of the guide 320 spaced away from a handle end 322, nearer the second end 324. Terminal ends of slot 331 and 333 are configured to limit blade motion along the tendon and thereby a length of graft formed. Slot ends 331 and 333 may act as a hard stop, preventing blade assembly 350 from extending beyond the guide 320 and unintentionally damaging tissue. During use, slot 330 may be placed over the targeted grafting portion and blade assembly 350 may then pierce the anterior surface of the tendon adjacent end 333 before moving between the two ends 331 and 333 to form lateral sides of a desired graft length. Slot 330 is shown as a single elongate opening. In an alternative embodiment (not shown) guide slot 330 may define a circuitous pathway for a blade to follow. For example, slot 330 may include a first longitudinal slot, a distal transverse slot adjacent end 324 and also a second longitudinal slot that may be parallel to the first longitudinal slot. The slot may be an elongate "U" shape. A single blade following the path defined by the "U" shaped slot may therefore guide a blade to form both lateral sides of the graft strip and truncate the end of the strip.

Once guide 320 has been placed, cutting may therefore be safely performed with minimal visualization. Guide 320 may therefore be provided as a series of guides having a variety of dimensions such as guide thicknesses T and slot lengths accordingly. Guide 320 may include a lower or posterior surface 332 that lies atraumatically on an anterior surface of QT and easily slides over the tendon anterior surface. Top surface 334 may also be smooth to aid insertion between patent tissues. Guide thickness T may be sufficient to cooperate with the blade assembly 350 to define a depth of cut into the tissue. This may limit depth of cut to mitigate risk of penetrating the knee capsule when paired with the intended blade.

Figure 4A:
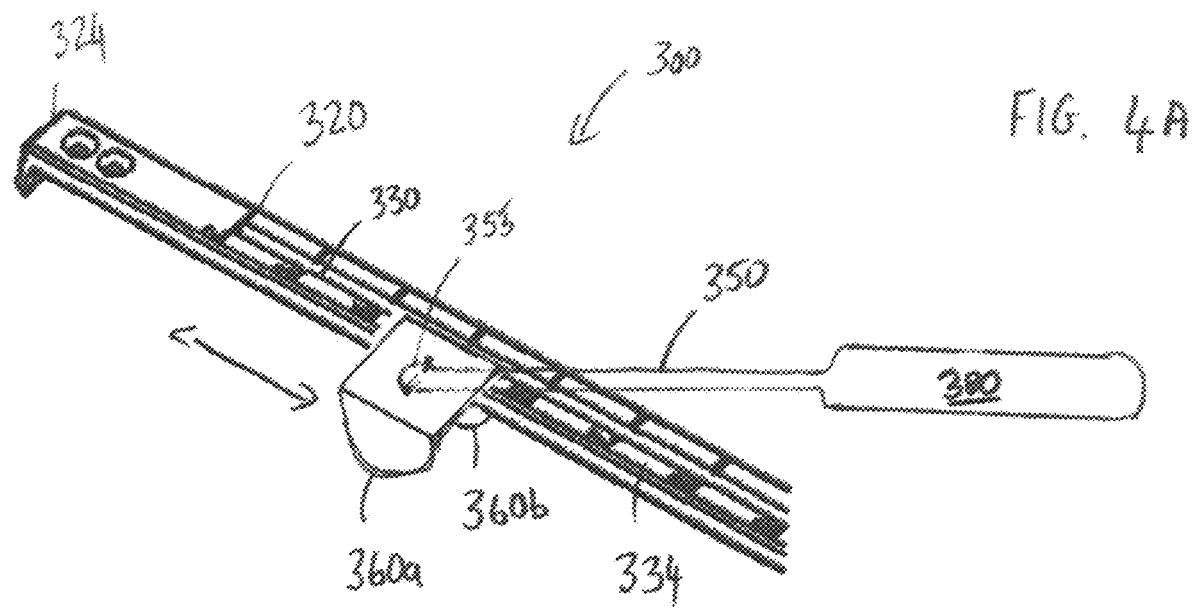
FIG. 4A schematically shows a tendon-harvesting system with a dual blade in accordance with at least some embodiments.
Figure 4B:
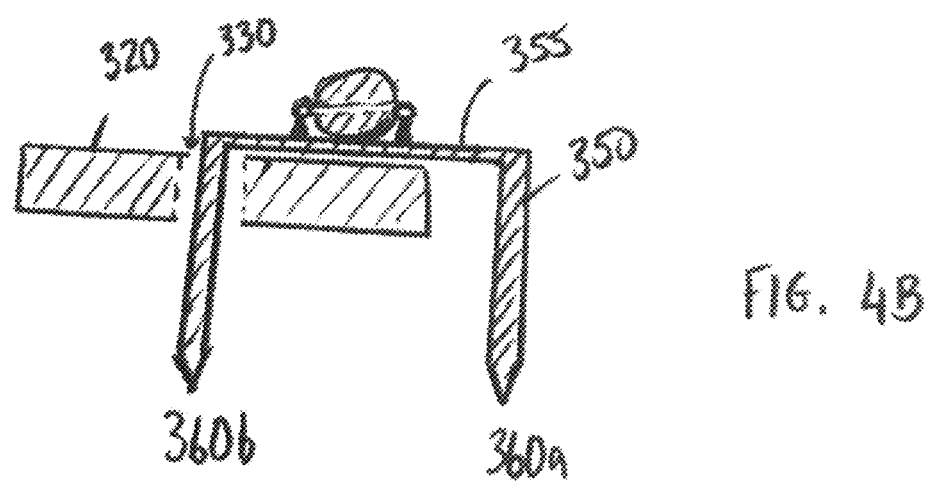
FIG. 4B schematically shows a cross section of the tendon-harvesting system of FIG. 4A, in accordance with at least some embodiments.

Shown in both FIGS. 4A and 4B, blade assembly 350 is configured to be selectively engageable and removable from guide 320. Blade 350 may include a flat top surface 355 that is smooth for easy sliding both between tissue layers, along guide top surface 334 and along slot 330. Blade 330 may be "U" shaped defining two cutting edges 360a and 360b so that movement of the blade assembly 350 along slot 330 may simultaneously create two parallel cuts into the tendon, defining a graft width. One of the blades 330 therefore extend through a slot 330 that is open through the entire thickness of the guide 320. Blade assembly 350 may include a handle 360 that may aid in sliding blade 350 along slot 330. Each blade assembly 350 may define arced or curved cutting edges 360a and 360b so that tissue may be cut while the blade assembly 350 moves both back and forth. Stated otherwise arced blade edges 360a and 360b each define a distal cutting edge and a proximal cutting edge. While advancing the blade assembly 350 towards the at least one tooth 325, the distal cutting edge may cut through the tendon and while retracting the blade 350 the proximal cutting edge may cut deeper through the tendon. As explained previously tendon may be a fibrous tissue, resistant to easy cutting and therefore several passes of the blade 350 may be preferred. These passes may be made more reliable and consistent by controlling the blade movements with the guide 320. In alternative embodiments, blade assembly 350 may define an energy-based device such as a shaver blade device, an ultrasonic cutting tool or electrosurgical device. These devices may transect the tough QT tissue more readily. Guide slot 330 may be sufficiently wide to receive an existing energy based device and may be up to 5 mm wide. Alternatively, a configuration similar to blade assembly 350 with cutting edges or a "U" shaped cross section may be configured to operatively couple to an energy based power supply and electro surgically cut tissue.

According to an exemplary method of the present invention, a graft may be harvested (sized and cut to specific dimensions) by the following steps: guide 320 may be inserted through a small incision above the kneecap of knee, under the skin and along an anterior surface of the QT. A mark 328 on the guide 320 corresponding with the desired graft length may be aligned with the superior pole of the patella and at least one tooth 325 of the guide 320 may then be anchored with an adjacent portion of the tendon tissue. Tooth 325 may be configured such that pressure from a user's hand may be sufficient to anchor tooth 325 within tissue. Pins or needles may then by pushed through patient's skin and through holes 372 and into the QT. A blade assembly 350 may be inserted into a slot 330 of the guide 320 and advanced along the slot 330, the blade assembly 350 having a first cutting edge along a first side of the blade and a second cutting edge along a second side of the blade; the first and second side continuous with each other forming an arced cutting edge. Alternatively, the blade assembly 350 may be an energy-based device such as a shaver style blade or electrosurgical device. Blade assembly 350 may slide along elongate slot 330, slot 330 defining the trajectory of blade assembly and thereby controlling a cut depth and trajectory into the QT. The blade assembly may then be retracted along the first opening 330 to further cut into the QT. Blade assembly 350 may include two laterally spaced blades that simultaneously create two cuts parallel to each other, defining a width of tendon graft. A first of the two laterally spaced blades may extend through a thickness of the guide through the slot 330. The other of the two laterally spaced blades may extend along or adjacent an outer lateralmost surface of the guide 320. The blade cooperates with a thickness of the guide 320 to define a depth of cut into the tendon. This method may include guiding the blade assembly using software guidance.

Figure 5A:
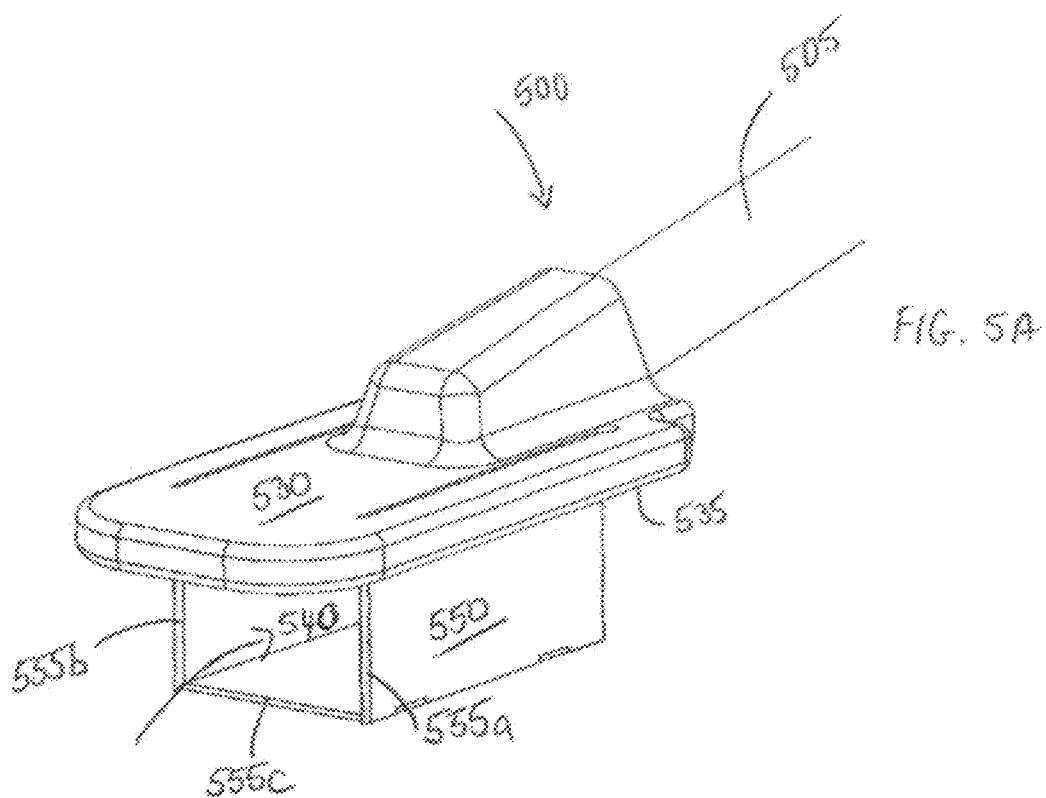
FIG. 5A-5C schematically show views of a further embodiment of a tendon harvesting assembly, in accordance with at least some embodiments.
Figure 5B:
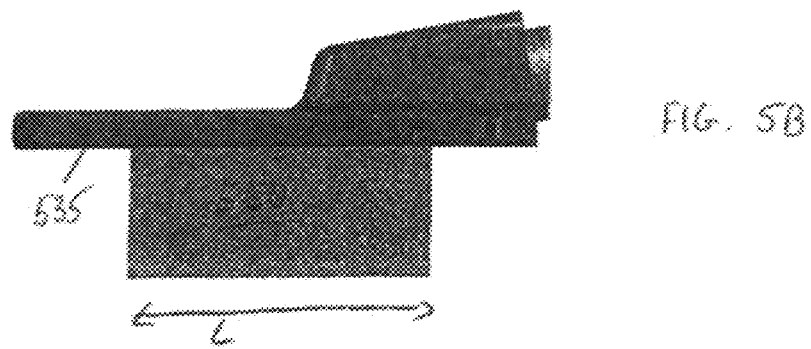
Figure 5C:
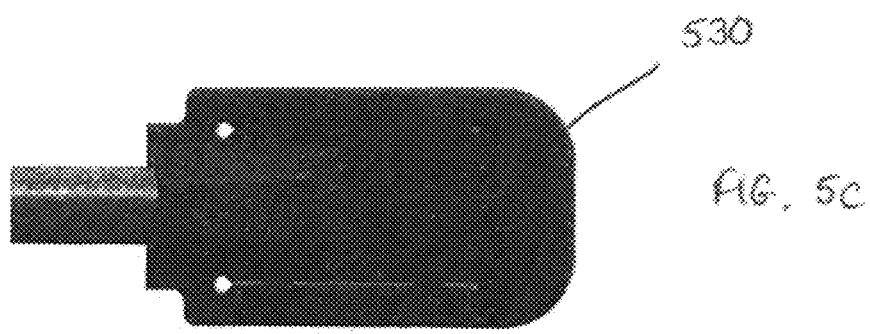

Guide 320 may also be used to guide cutting of the bone block portion of a graft, wherein the QT is removed with a portion of patella still attached. Guide 320 may be placed so that teeth 325 are flip up and through holes 372 placed on top of patella. Guide longitudinal axis may be parallel with and coaxial with graft longitudinal axis. Needles or guide wires may then be placed through holes 372 and into a portion of patella to stabilise the guide 320 while forming a bone block FIGS. 5A-5C schematically show an alternative embodiment of a QT harvesting tool 500, including a handle 505 or rod, with a blade guide 530 and blade 550 at a distal end. Handle 505 may be selectively removable from blade guide 530 and may be a reusable handle, configured to be sterilized and with a universal attachment means for attachment to several tool-working ends during a procedure. Blade guide 530 defines a surface 535 that is configured to engage and slide along a top or anterior surface of QT, to limit motion of the blade 550 into the QT. Blade 550 extends posteriorly from surface 535 and may include two edge surfaces 555a and 555b, which may extend perpendicularly from surface 535, with a connecting edge surface 555c therebetween. Edge surface 555c may lie parallel to surface 535. At least one of the edge surfaces may be configured to cut. In some example embodiments, all edge surface 555a, 555b and 555c are configured to cooperate and cut a defined shape of graft in this case a rectangular shape. In alternative embodiments, edge surfaces 555a, 555b and 555c may be oriented to cut a different pre-defined shape such as a quadrilateral, rhombus, trapezoid or square from example. Edge surfaces 555a, 555b and 555c may also be curves edges, and cut a more curved or rounded graft. In some alternative embodiments, the lateral sides of the graft may be cut using a device such as the embodiments shown in FIG.

Seen in FIG. 5B, blade 550 has a length "L" that may help stabilize the structure of the blade to resist deformation from the tough QT tissue. Along length "L" cross section defined by 555a, 555b and 555c is shown as constant. However in alternative embodiments opening 540 may taper to a gradually larger opening size from the cutting edges so the graft tissue may be cut at the cutting edges 555a, 555b and 555c and then extend though opening 540 with minimal interference from the blade walls.

Surface 535, extends further laterally and axially than blade 550, so as to provide stability while sliding the blade along the QT anterior surface and maintain the desired path of the blade 550. Stated otherwise blade cutting surfaces 555a and 555b are laterally spaced a first distance so as to define a width of QT graft corresponding to the first distance, and wherein the guide surface 535 has a width that extends further laterally than the lateral spacing of cutting surfaces 555a and 555b. The guide surface therefore has a width that is greater than the first distance. Blade cutting edges 555a and 555b are disposed on opposing sides of a longitudinal axis of harvesting tool 500. A method of harvesting a QT with device embodiment as shown in FIGS. 5A-5C, including first dissecting fatty tissue from QT/surrounding musculature and identifying a desired QT trajectory. The QT is then separated at the proximal pole of patella and a whipstitch placed through the QT, a suture tail extending from the whipstitch. The suture tail is then fed through the opening 540 in the blade, the opening defined by a first, second and third cutting edge. The graft is prepared using a combination of tension to suture tails to draw QT into the opening 540 while pushing and sliding/guiding blade along QT. A guide surface 535 may slide along an anterior surface of QT and blade 550 creates incisions.

Figure 6A:
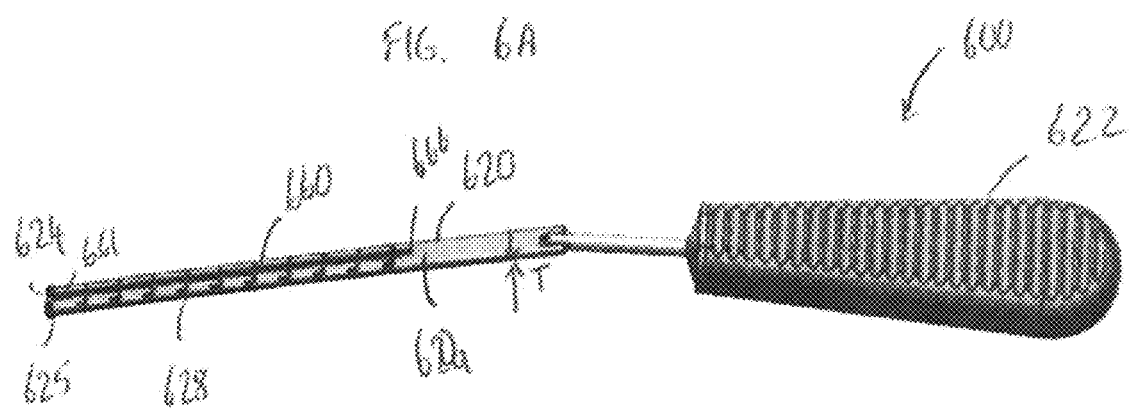
FIGS. 6A and 6B schematically show perspective views of a tendon-harvesting guide, in accordance with at least some embodiments.
Figure 6B:
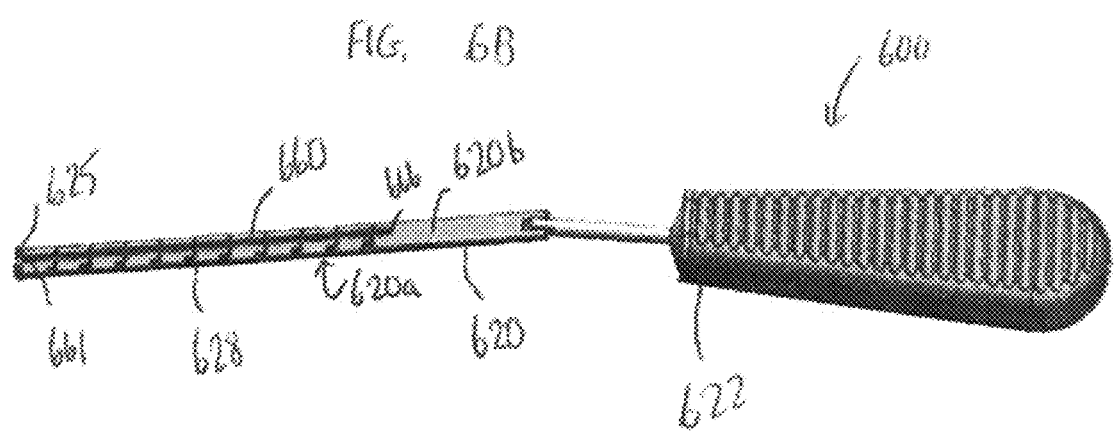

A fourth example embodiment is shown in FIGS. 6A and 6B with reference to the embodiment described in FIGS. 3, 4A and 4B. This embodiment is configured to allow the guide to operate in two orientations depending on the surgeon preference and which patient leg is chosen, the two orientations flipped relative to each other. They may be flipped in order to be left or right justified. Similar to a previous embodiment, this ruler 600 generally includes a blade guide 620, which may cooperate with a blade assembly such as 350 or 750 selectively coupled to the guide 620. Blade guide 620 is generally an elongate slotted ruler having a first end 622 that may include a handle and a second end 624. Guide 620 may include a means to engage or anchor with tissue disposed along its length, configured to inhibit the guide 620 from unintentionally sliding or migrating over the tendon during use. As shown guide 620 includes at least one tooth 625 at the second end 624. Tooth may be similar to embodiment shown in FIG. 3. This embodiment may be flipped to operate on either side and therefore there may be teeth on both the top surface 620a and bottom surface 620b. Bottom surface 620b may be a posterior surface that engages the QT in some orientations such as the orientation in FIG. 6A, or a top surface in a flipped orientation (FIG. 6B). Having the tooth 625 at an end of the guide 620, rather than along the length may be preferable to limit any potential damage caused by the tooth 625 to the graft to an area that may be easily removed or not form part of the graft itself and therefore maintain good viability of the resulting graft. Tooth 625 may be configured to pierce the tendon, and may have a length extending approximately equivalent to or less than a targeted graft thickness. In some embodiments, similar to the embodiment disclosed in FIGS. 3 and 4A for example, tooth 625 may be configured alternatively in that the at least one tooth length may be approximately the same as a blade extension (Y) below the first surface 620a or second surface 620b. Alternative embodiments may include a plurality of teeth. In addition to or alternatively a high friction surface along a portion of first of guide 620 in addition to or instead of teeth may aid in maintaining the location or guide 620 on the slippery anterior surface of QT Guide 620 may also include a series of marks 628 on at least one of the first and second surface 620a, 620b, indicating inches or some equivalent measurement units for visual feedback on a depth of insertion of the guide 620 into an incision and along the tendon. Marks 628 may also be used for estimating a graft cut length and therefore may indicate distances along the slot or opening 660 and not from a distal-most end of guide 620. As shown slot 660 does not necessarily originate from the distal-most end of guide 620; end 661 is spaced away from end 624. For example in use, during insertion of guide 600 between tissues and over the QT, mark 628 corresponding with the desired graft length may be aligned with the superior pole of the patella and the at least one tooth 625 may then be anchored with an adjacent portion of the tendon tissue.

Figure 3A:
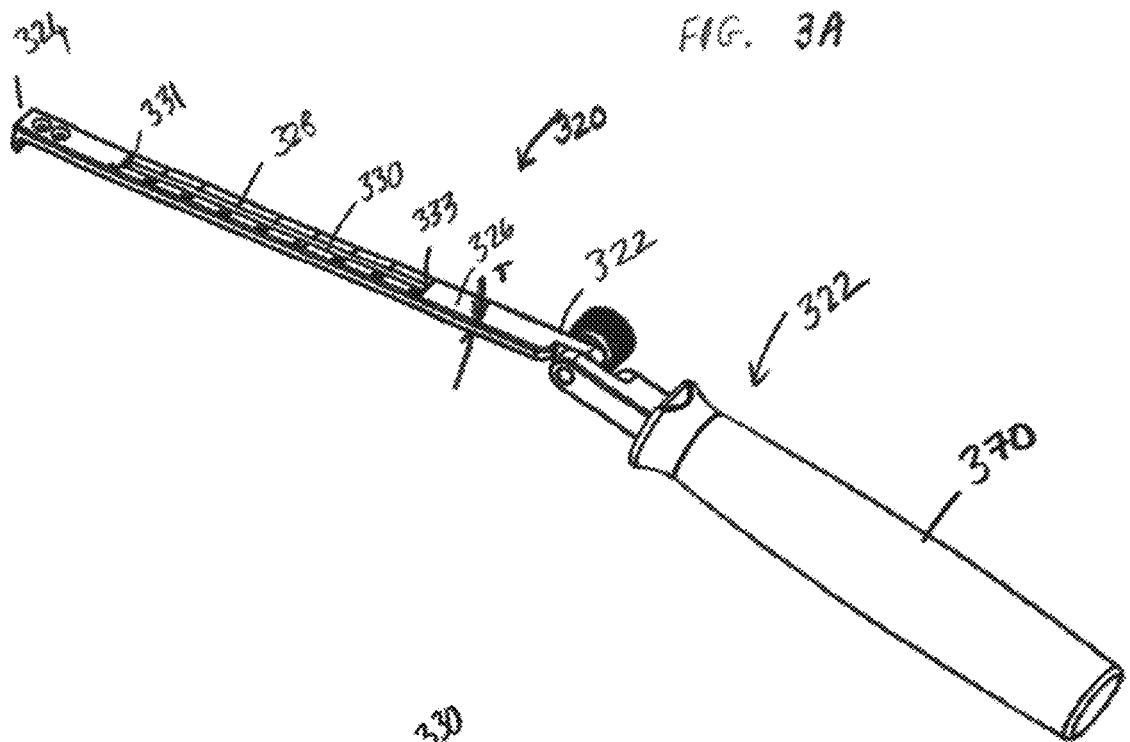
FIGS. 3A-3C schematically show views of a tendon-harvesting guide in accordance with at least some embodiments.
Figure 3B:
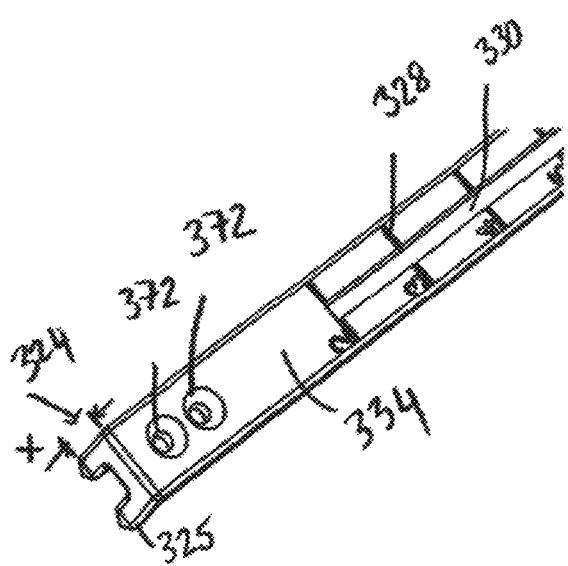
Figure 3C:
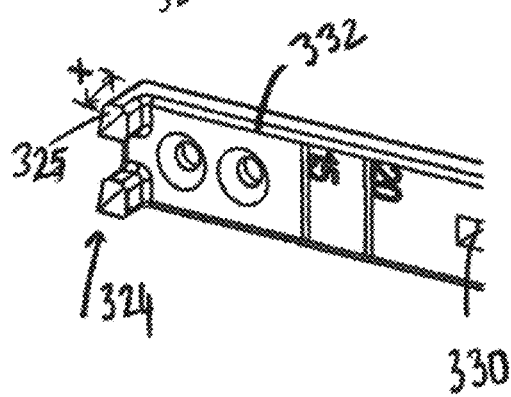

Similar to the embodiment in FIGS. 3A-3C, slot 660 may extend through the entire thickness of the guide 620. Slot 660 may aid in maintaining a direction and trajectory of a blade assembly such as blade assembly 350. Slot 660 may be sufficiently wide to receive a portion of a cutting tool such as blade assembly 350 or 750 and allow blade assembly 350 or 750 to move therealong. Slot 660 may however be sufficiently narrow to limit lateral motion of a cutting blade while the blade slides. Slot 660 as shown may extend along a portion of the guide 620, similar to the guide track portion described in earlier embodiments, the slot 660 predominantly biased or disposed towards a half of the guide 620 spaced away from a handle end 622, nearer the second end 624. Terminal ends of slot 661 and 666 are configured to limit blade motion along the tendon and thereby a length of graft formed. Slot ends 661 and 66 may act as a hard stop, preventing blade assembly 650 from extending beyond the guide 620 and unintentionally damaging tissue. Slot 660 may be parallel to a longitudinal axis of guide 600, and offset laterally from the longitudinal axis. Justification of the slot 660 to one side may provide better visualization of cutting markers 628 and also the cutting blades.

During use, slot 660 may be placed through a small incision near the patella, under the skin along the QT. Blade assembly 350, 750 may then move between the two ends 661 and 666 to form the desired graft length. Once guide 620 has been placed, cutting may therefore be performed with minimal visualization, as some of the guide 600 may be obscured by the patient's skin. Guide 620 may therefore be provided as a series of guides having a variety of dimensions such as guide thicknesses and slot lengths accordingly. Guide thickness T may be sufficient to cooperate with the blade assembly 350 to define a depth of cut into the tissue. This may limit depth of cut to mitigate risk of penetrating the knee capsule when paired with the intended blade. Guide 600 may be formed by injection molding and/or may be formed of a disposable single use material typically plastic. Guide handle 622 may be hingedly attached to the ruler 620, and may be removeably coupled to the ruler 620. Having a hinged attachment may allow the handle to be moved away from the surgeon's field of view.

According to an exemplary method of the present invention, a graft may be harvested (sized and cut to specific dimensions) by the following steps: a surgeon may chose a justification or side of the flip ruler guide 620. Guide 620 may be inserted through a small incision above the kneecap of knee, under the skin and along an anterior surface of the QT in this chosen justification. A mark 628 on the guide 620 corresponding with the desired graft length may be aligned with the superior pole of the patella and at least one tooth 625 of the guide 620 may then be anchored with an adjacent portion of the tendon tissue. Tooth 625 may be configured such that pressure from a user's hand may be sufficient to anchor tooth 625 within tissue. A blade assembly such as blade assembly 350 may be inserted into an opening or slot 660 of the guide 620 and advanced along the opening 660. Blade assembly 350 may slide along elongate opening or slot 660, slot 660 defining the trajectory of blade assembly and thereby controlling a cut depth and trajectory into the QT. The blade assembly may then be retracted along the first opening 660 to further cut into the QT. The blade cooperates with a thickness of the guide 620 to define a depth of cut into the tendon. The offset slot 660 of the guide allows the surgeon to view the markings 628 and blade assembly as it translates along the guide 620.

An embodiment of a pivoting blade assembly is shown in FIG. 7A-7D that may be used with ruler guide such as that shown in FIGS. 3A-3C or 6A and 6B. This pivoting blade assembly 750 provides a means of creating cuts of consistent depth in the QT regardless of the angle the user orients the handle. Blade assembly 750 allows independent rotation of the handle 780 while the blade orientation remains constant. When using an off-the-shelf scalpel for example, where the handle is fixedly coupled at a fixed orientation to the blade, a depth of cut is dictated by the angle at which the surgeon introduces and holds the blade to the surface of the soft tissue. In cases where access to the soft tissue is limited by surrounding skin/fat, such as in minimally invasive quadriceps tendon soft tissue harvests, restricted access to parts of the tendon may result in inconsistent overall tendon thickness with a fixed handle such as an off-the-shelf scalpel.

Figure 7A:
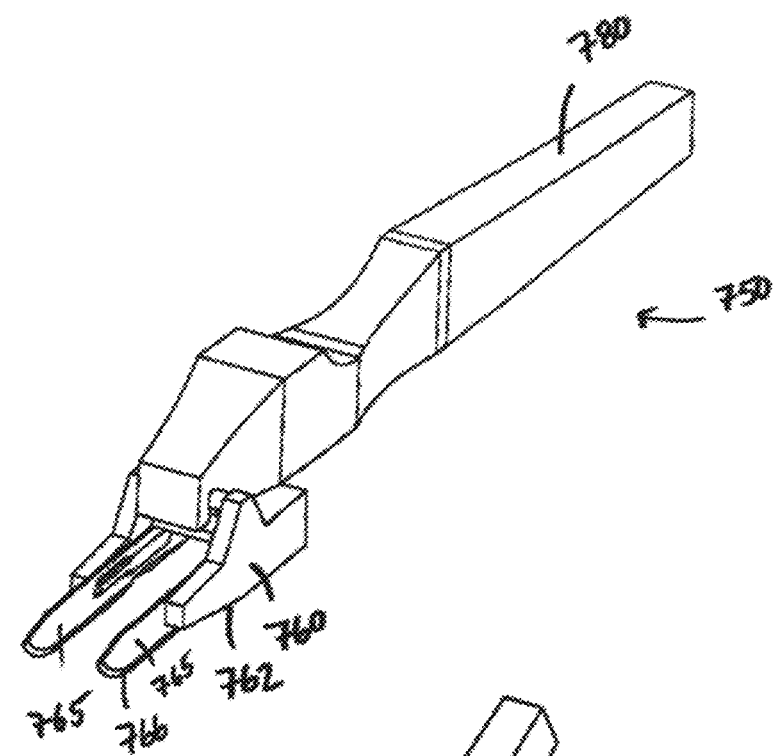
FIG. 7A-7D show a variety of views of a blade assembly in accordance with at least some embodiments.
Figure 7B:
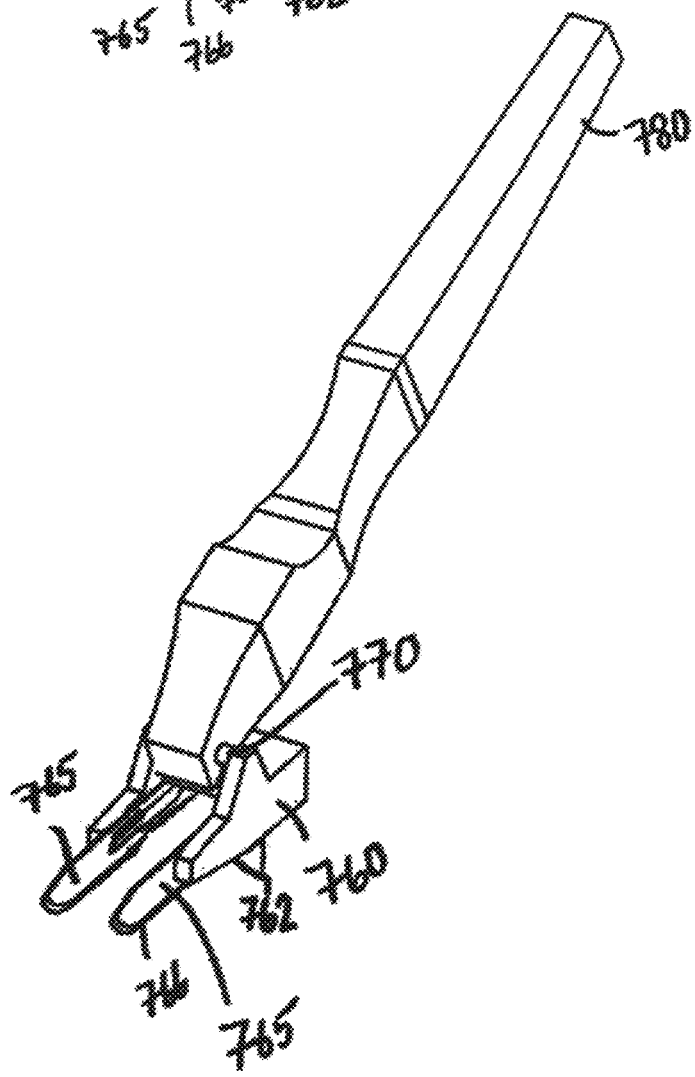
Figure 7C:
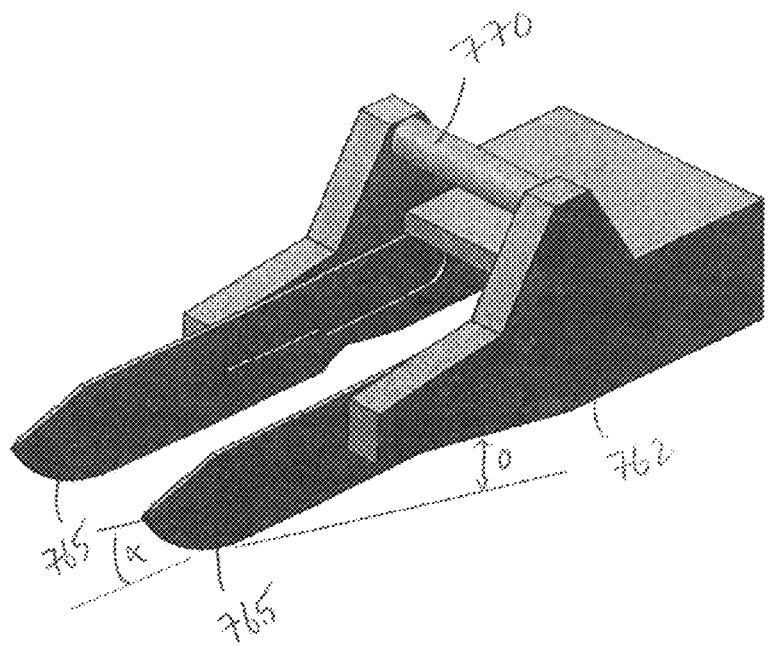
Figure 7D:
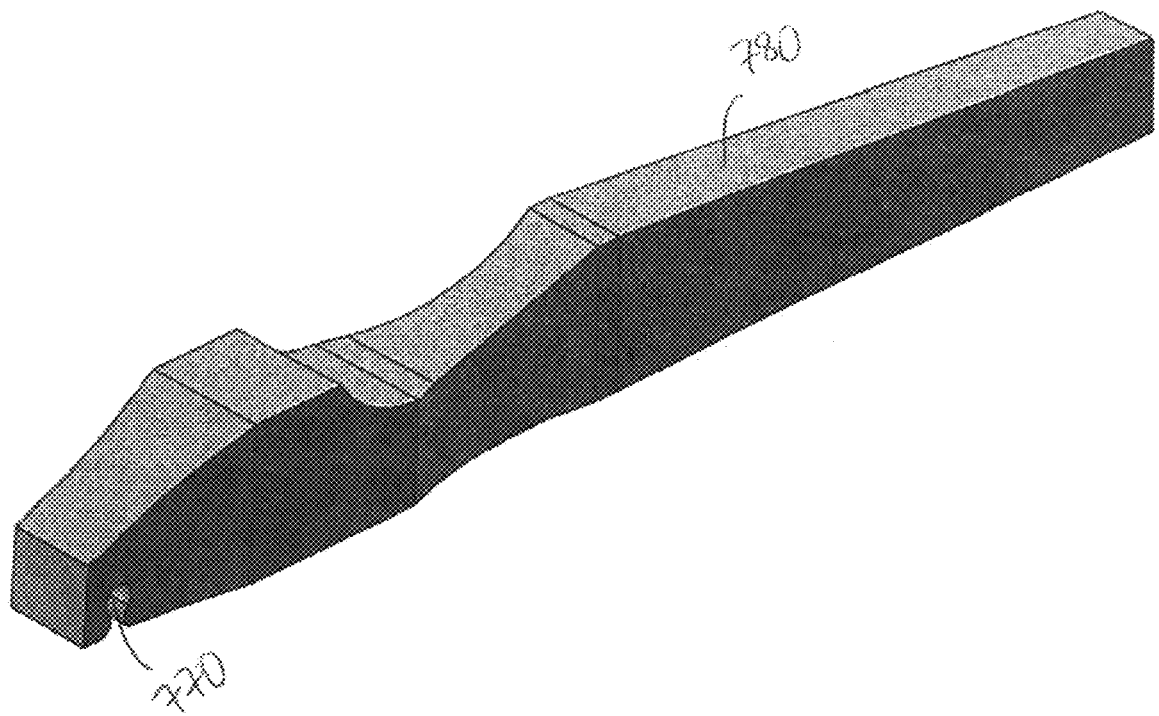

Blade assembly 750 generally includes a handle 780 pivotally coupled to a blade portion 760. Handle 780 may be selectively removable from blade portion 760. Handle 780 may be pivotally coupled by a pin joint, for example. Handle 780 may be independently rotated relative to blade end 760, while still translating blade end along the QT. Blade portion 760 may include at least one surface 762 for sliding along a surface such as ruler surface 326 for example in FIG. 3A or 620*a* or 620*b* in FIG. 6A, to limit a depth of cut into the QT. Surface 762 may define a planar flat surface that is configured to maintain a constant depth of penetration of the blade leading edge 766 into the QT. Surface 762 may therefore be offset ("O") and/or angled a relative to blade leading cutting edge. Offset "O" is at least as thick as ruler guide 620 so as extend through slot of ruler guide 620 and penetrate QT. Blade portion 760 may include means to couple to standard off the shelf blades 765. FIG. 7A shows the handle 780 in a more horizontal orientation relative to the blade portion 760, which may be the preferred orientation at a cranial end of the QT, when the system 750 is at least partially threaded under the patient's skin. FIG. 7B shows the handle 780 in a more vertical orientation relative to the blade portion 760, which may be the preferred orientation at a patella end of the QT, when the system is closest to the incision and initially penetrating the QT. Due to the pivot or hinged connection 770, surface 762 may remain in contact with a ruler guide such as ruler guide 620, for a range of handle orientations.

In some alternative embodiments, there may be only one blade as opposed to the double-bladed design disclosed herein. In some alternative embodiments, the rotation of the blade portion may be actively controlled. For example a blade which is free to pivot can be seen as a risk, and so having some control feature, such as a spring which can be overcome to pivot at a low force, or a lock. Spring may be coupled between the handle 780 and blade portion 760. An alternative embodiment could be a rotation-controlled pivot, which changes the depth of cut as the angle increases. In other alternative embodiments, a locking feature to lock the distal tip in a certain orientation may be provided.

Figure 8A:
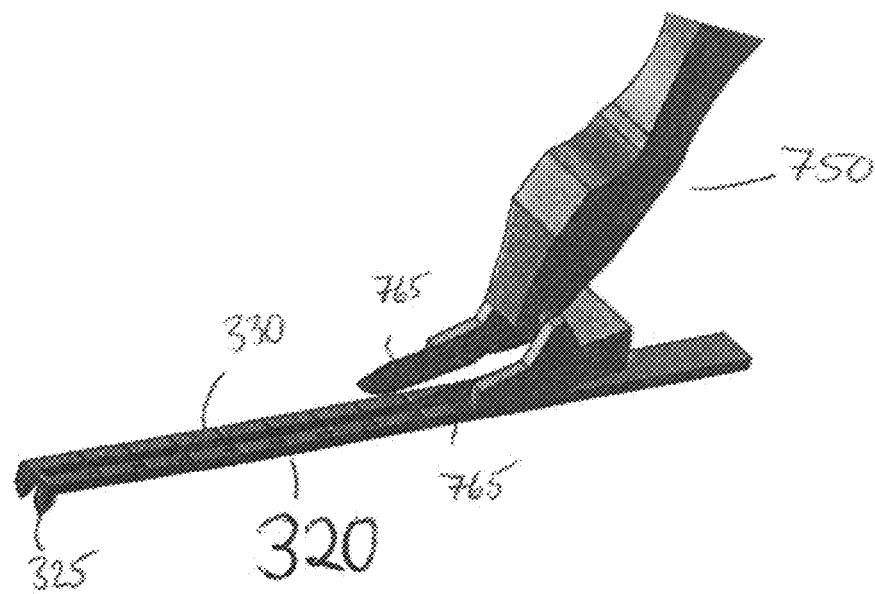
FIGS. 8A and 8B show a tendon-harvesting system in accordance with at least some embodiments.
Figure 8B:
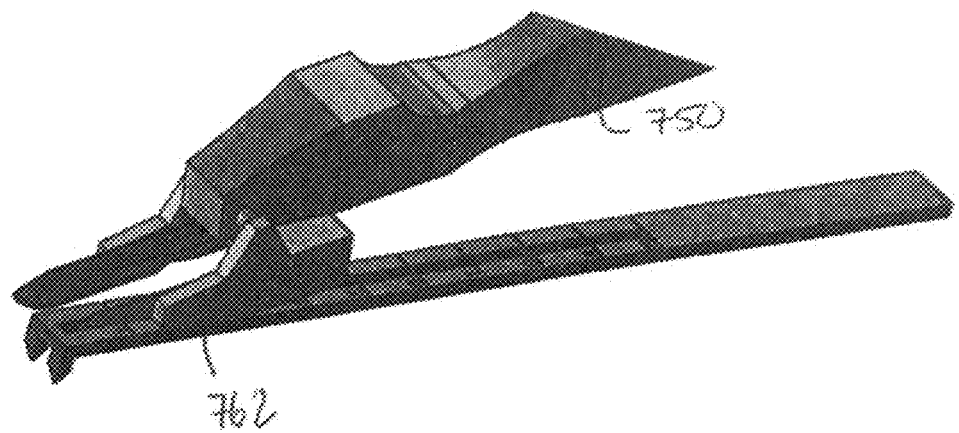

According to an exemplary method of the present invention and represented in FIGS. 8A and 8B, a graft may be harvested (sized and cut to specific dimensions) by the following steps: guide 600 or 320 may be inserted through a small incision above the knee cap of knee, under the skin and along an anterior surface of the QT. A mark 328 or 628 on the guide 320 or 600 corresponding with the desired graft length may be aligned with the superior pole of the patella and at least one tooth, such as tooth 325 of the guide 320 may then be anchored with an adjacent portion of the tendon tissue. Tooth 325 may be configured such that pressure from a user's hand may be sufficient to anchor tooth 325 within tissue. Depending on the justification preferred by the surgeon, guide 600 with an offset slot 660 may be flipped to better visualize markings 628 and slot 660. A blade assembly such as blade assembly 750 may include two blades 765, one of with may be inserted into an opening or slot 330 of the guide 320 (or 660 of guide 600) and advanced along the slot 330. A surface 762 that may define a flat planar surface may engage a top surface of guide 320 or 600. Blade assembly 750 may slide along elongate slot 330, slot 330 defining the trajectory of blade assembly. Surface 762 may slide along guide top surface and thereby control a cut depth and trajectory into the QT. Blade assembly 750 may slide along elongate slot 330, from a first location adjacent the incision and patella, with handle 780 in a first orientation, handle 780 then moving the blade portion 760 along the guide 320 or 600, maintaining a constant orientation of the blades and thereby the QT cut depth while the handle orientation changes from the first orientation to a different orientation (FIG. 8B). The first orientation may be more vertical and the different orientation maybe more horizontally disposed. Handle may pivot relative to blade portion while moving along guide 320 or 600 while keeping surface 762 engaged with guide top surface. The blade assembly 750 may then be retracted along the first opening 330 or 660 to further cut into the QT.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

We claim:

1. A tendon harvesting system for harvesting a target length a target width and a target thickness of a tendon tissue comprising:
    a blade assembly defining a "U" shaped channel and including two cutting blades that are laterally spaced from each other to define ends of the "U" shaped channel; and
    a guide having an elongate body defining a handle end and free end and a longitudinal axis the elongate body having a lower surface and an elongate body thickness;

wherein the elongate body is configured to engage with the "U" shaped channel of a blade assembly and guide a trajectory of the two cutting blades of the blade assembly along the elongate body and thereby define the target length of the tendon tissue to be harvested, and wherein the elongate body is configured to cooperate with the "U" shaped channel to position the two cutting blades below the lower surface and into the tendon tissue, the "U" shaped channel and elongate body thickness defining a target cutting depth into the tendon tissue as the blade assembly translates along the tendon tissue, thereby defining the target width and the target thickness of the tendon tissue to be harvested.

2. The tendon harvesting system of claim 1 wherein the elongate body includes a series of marks therealong, for estimating the target length of the tendon tissue to be harvested, and wherein the series of marks are disposed along a top surface of the guide and spaced away from surfaces of the guide that are configured to engage the "U" shaped channel of the blade assembly, as the blade assembly translates along the tendon tissue.

3. The tendon harvesting system of claim 2 wherein the series of marks are configured to estimate the target length by aligning a first mark of the series of marks relative to a superior pole of a patella.

4. The tendon harvesting system of claim 1 wherein the lower surface is configured to engage an anterior surface of the tendon tissue.

5. The tendon harvesting system of claim 1 wherein the two cutting blades each define a continuously curved cutting edge, configured to cut into the target tendon while both advancing and retracting along the tendon.

6. The tendon harvesting system of claim 1 wherein the blade assembly includes a handle for translating the two cutting blades along the guide and wherein the blade assembly is configured to maintain a consistent cut depth during translation for a range of orientations of the handle relative to the guide elongate body.

7. The harvesting system of claim 1 wherein the "U" shaped channel of the blade assembly is configured to wrap around three sides of the elongate body to limit lateral motion of the blade assembly as the two cutting blades translate along the tendon tissue.

8. A tendon harvesting system for harvesting a length of tendon tissue comprising:
a blade guide having a handle end and a guide end extending therefrom, the guide end defining a planar surface for engaging a top surface of the tissue; the guide end including an elongate opening; and
a blade assembly including two cutting blades laterally spaced from each other, the blade assembly configured to slide along the elongate opening with one of the two cutting blades extending through and below the elongate opening and into the tendon tissue, the blade assembly and guide end configured to cooperate and control a trajectory of the two cutting blades into and along the tissue, wherein the blade guide includes an elongate body configured to be received within a "U" shaped portion of the blade assembly, the "U" shaped portion defining two ends, defined by the two cutting blades.

9. The harvesting system of claim 8 wherein the blade assembly includes a handle, configured to slide the blade assembly along the elongate opening, and wherein while sliding, the handle rotates through a range of angles relative to the guide, and wherein the blade assembly is configured to maintain a constant extension of the two cutting blades into the tendon tissue while rotating the handle through die range of angles.

10. The tendon harvesting system of claim 8 wherein the guide end includes a first and a second stop surface, the first stop surface configured to limit translation of the two cutting blades at a first end of the tendon tissue, and the second stop surface configured to limit translation of the two cutting blade at a second, opposing end of the tendon tissue, the first and second stop surface defining a maximum length of tendon tissue to be harvested.

11. The tendon harvesting system of claim 8 wherein the blade guide includes a series of marks therealong, for estimating the length of tissue to be harvested.

12. The tendon harvesting system of claim 8 wherein the two cutting blades each define a continuous curved cutting edge.

13. A method of harvesting a graft comprising:
inserting a guide portion of a blade guide through an incision and along an anterior surface of a quadriceps tendon (QT);
inserting a first cutting blade of a blade assembly through a first end of an elongate opening of the guide portion and into the anterior surface of the QT; and
slidingly engaging a surface of the blade assembly along the guide portion while advancing the first cutting blade through and along the elongate opening to a second, opposing end of the elongate opening and thereby forming a first elongate side of the graft, the surface of the blade assembly configured to cooperate with the guide portion to limit a depth of penetration of the first cutting blade into the QT.

14. The method of claim 13 further comprising rotating a handle of the blade assembly through a range of angles relative to the QT while advancing the first cutting blade, and maintaining a constant depth of penetration of the first cutting blade, while rotating and advancing.

15. The method of claim 13 wherein the blade assembly comprises a second cutting blade parallel to and laterally offset from the first cutting blade, and wherein advancing the first cutting blade simultaneous advances the second cutting blade and forms the first and a second elongate side of the graft.

16. The method of claim 13 wherein inserting the guide portion through the incision further comprises aligning a mark of a plurality of marks on the guide portion with a superior pole of the patella and estimating a length of the graft using the plurality of marks.

17. The method of claim 16 wherein slidingly engaging a surface of the blade assembly includes a surface absent the plurality of marks thereon.

* * * * *